US012020351B2

United States Patent
Hu et al.

(10) Patent No.: US 12,020,351 B2
(45) Date of Patent: Jun. 25, 2024

(54) METHOD, DEVICE AND EQUIPMENT FOR RECONSTRUCTING PET IMAGES

(71) Applicant: SHENZHEN INSTITUTES OF ADVANCED TECHNOLOGY, Shenzhen (CN)

(72) Inventors: Zhanli Hu, Shenzhen (CN); Hairong Zheng, Shenzhen (CN); Dong Liang, Shenzhen (CN); Xin Liu, Shenzhen (CN); Yongfeng Yang, Shenzhen (CN); Dongfang Gao, Shenzhen (CN)

(73) Assignee: SHENZHEN INSTITUTES OF ADVANCED TECHNOLOGY, Shenzhen (CN)

(*) Notice: Subject to any disclaimer, the term of this patent is extended or adjusted under 35 U.S.C. 154(b) by 395 days.

(21) Appl. No.: 17/433,081

(22) PCT Filed: Dec. 18, 2020

(86) PCT No.: PCT/CN2020/137542
§ 371 (c)(1),
(2) Date: Aug. 23, 2021

(87) PCT Pub. No.: WO2022/126581
PCT Pub. Date: Jun. 23, 2022

(65) Prior Publication Data
US 2022/0319069 A1    Oct. 6, 2022

(51) Int. Cl.
*G06T 11/00* (2006.01)
*A61B 6/03* (2006.01)
*G06V 10/77* (2022.01)

(52) U.S. Cl.
CPC ............ *G06T 11/006* (2013.01); *A61B 6/037* (2013.01); *G06T 11/008* (2013.01); *G06V 10/7715* (2022.01); *G06T 2211/40* (2013.01)

(58) Field of Classification Search
None
See application file for complete search history.

(56) References Cited

U.S. PATENT DOCUMENTS

| | | | | |
|---|---|---|---|---|
| 11,810,292 | B2 * | 11/2023 | Madabhushi | ....... G06F 18/2413 |
| 2010/0172555 | A1 * | 7/2010 | Hasezawa | ............ G06V 10/772 382/128 |

(Continued)

FOREIGN PATENT DOCUMENTS

| | | |
|---|---|---|
| CN | 108805892 A | 11/2018 |
| CN | 110838173 A | 2/2020 |
| CN | 111402357 A | 7/2020 |

OTHER PUBLICATIONS

Martin Carrier-Vallières, "FDG-PET/MR Imaging for Prediction of Lung Metastases in Soft-Tissue Sarcomas of the Extremities by Texture Analysis and Wavelet Image Fusion," MS Thesis, McGill University, Dec. 2012 (Year: 2012).*

(Continued)

*Primary Examiner* — Soo Shin
(74) *Attorney, Agent, or Firm* — Harness, Dickey & Pierce, P.L.C.

(57) ABSTRACT

A method, device and equipment for reconstructing a PET image are provided. The method includes acquiring a prior image comprising an anatomical image and an autocorrelation feature image, the autocorrelation feature image being determined based on gray-level co-occurrence matrix of the anatomical image; and acquiring a feature value of the prior image; reconstructing the PET image according to the feature value and an iterative algorithm.

8 Claims, 5 Drawing Sheets

(56) References Cited

U.S. PATENT DOCUMENTS

2016/0260211 A1\* 9/2016 Gillies .................... A61B 6/50
2018/0342058 A1\* 11/2018 Madabhushi ........ G06V 10/255
2019/0355157 A1\* 11/2019 Daniel ............... G01R 33/5611
2020/0401938 A1\* 12/2020 Etkin .................... G16H 50/30

OTHER PUBLICATIONS

International Search Report issued in PCT/2020/137542, dated Jun. 24, 2021.

\* cited by examiner

METHOD, DEVICE AND EQUIPMENT FOR RECONSTRUCTING PET IMAGES

CROSS-REFERENCE TO RELATED APPLICATIONS

This application is a 371 U.S. National Phase of International Application No. PCT/CN2020/137542 filed on Dec. 18, 2020. The entire disclosures of the above application is incorporated herein by reference.

FIELD

The present disclosure relates to the field of PET imaging technology, and in particular to a method, device and equipment for reconstructing PET images.

BACKGROUND

PET (Positron Emission Tomography) can reflect metabolic processes of organisms in vivo by using a radiotracer, so as to carry out a non-invasive imaging. It can be used for early clinical tumor detection, tumor treatment evaluation and pharmacokinetic analysis and so on. The image reconstruction for low-count PET projection data can not only reduce injection dose of the radiotracer, scan time and economic cost, but also improve the time resolution of dynamic PET, which is of great significance in clinical applications. However, low-count PET reconstruction will result in a reconstructed image with high noise and low signal-to-noise ratio, as it is an ill-conditioned inverse estimation problem, which is difficult to solve. Therefore, it will have an important scientific significance for clinical applications of PET important to study the low-count PET reconstruction algorithms.

In related art, the quality of reconstructed PET images can be improved based on the prior information of MRI (Magnetic Resonance Imaging) anatomical images. There are two main implementations in the related art: one refers to using the penalty likelihood function framework to introduce the prior information into the target likelihood function through a penalty term in order to realize the reconstruction of the PET image; the other refers to introducing similarity of MRI gray values around voxels of MRI anatomical image as anatomical prior information into the orthographic projection process for reconstructing PET, and then carrying out an iterative reconstruction through the classic expected maximum algorithm to obtain the reconstructed PET image.

SUMMARY

EmbodA method, a device, and an equipment for reconstructing PET images, to solve the problem of PET images with poor quality and highly noisy reconstructed based on the prior information in the related art.

The present disclosure is implemented in this way.

In a first aspect, a method for reconstructing a PET image is provided, comprising: acquiring a prior image comprising an anatomical image and an autocorrelation feature image, the autocorrelation feature image being determined based on a gray-level co-occurrence matrix of the anatomical image; and acquiring a feature value of the prior image; and reconstructing the PET image according to the feature value and an iterative algorithm.

In a second aspect, a device for reconstructing a PET image is provided, comprising: a first acquisition module configured to acquire a prior image comprising an anatomical image and an autocorrelation feature image, the autocorrelation feature image being determined based on a gray-level co-occurrence matrix of the anatomical image; a second acquisition module configured to acquire a feature value of the prior image; and a reconstruction module configured to reconstruct the PET image according to the feature value and an iterative algorithm.

In a third aspect, an equipment is provided, wherein the equipment comprises: a memory, a processor, and a computer program stored on the memory and executable by the processor, the computer program, when executed by the processor, implementing the steps of the method described in the first aspect.

In a fourth aspect, a computer-readable storage medium is provided, storing a computer program that, when executed by a processor, implements the steps of the method described in the first aspect.

BRIEF DESCRIPTION OF THE DRAWINGS

The drawings described herein are provided for further understanding the disclosure and as a part of the disclosure. The exemplary embodiments of the disclosure and description thereof are used to explain the disclosure and not as any improper limitation to the disclosure. In the drawings.

Corresponding reference numerals indicate corresponding parts throughout the several views of the drawings.

DETAILED DESCRIPTION

Example embodiments will now be described more fully with reference to the accompanying drawings.

In order to make the purposes, technical solutions and advantages of the disclosure apparent, the technical solutions of the disclosure will be clearly and completely described below with reference to the specific embodiments and the corresponding drawings. It is obvious that the described embodiments are merely part of the embodiments of the disclosure rather than all the embodiments. Based on the embodiments in the disclosure, all the other embodiments obtained by a person skilled in the art without paying creative work will fall into the protection scope of the disclosure.

Technical solutions provided by embodiments of the present disclosure will be described below in detail with reference to the accompanying drawings.

Figure 1:
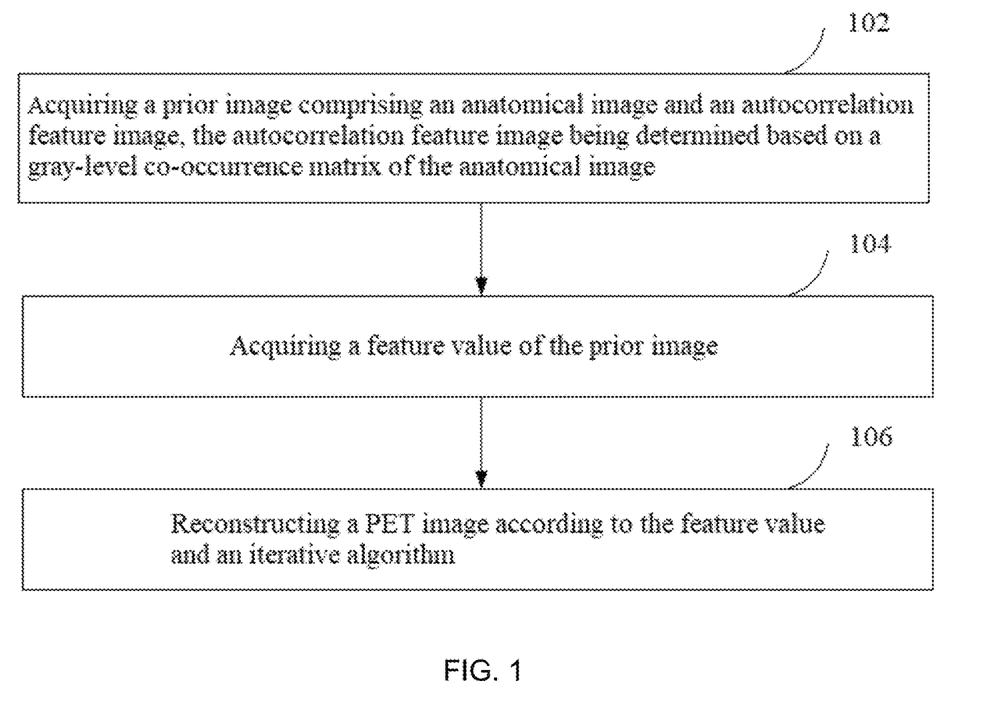
FIG. 1 is a schematic flowchart of a method for reconstructing a PET image provided by an embodiment of the present disclosure.

With reference to FIG. 1, FIG. 1 is a method, device and equipment for reconstructing a PET image provided by an embodiment of the present disclosure. As shown in FIG. 1, the method comprises the following steps.

Step 102: acquiring a prior image comprising an anatomical image and an autocorrelation feature image, the autocorrelation feature image being determined based on a gray-level co-occurrence matrix of the anatomical image.

Step 104: acquiring a feature value of the prior image.

Step 106: reconstructing the PET image according to the feature value and an iterative algorithm.

In this embodiment, the anatomical image may specifically be an anatomical image of MRI.

After acquiring the anatomical image, the prior image can be acquired based on the anatomical image in this embodiment. Different from the prior information in the related art, the prior image in this embodiment comprises the anatomical image and the autocorrelation feature image, wherein the autocorrelation feature image is determined according to the gray-level co-occurrence matrix of the anatomical image.

In one embodiment, after acquiring the anatomical image, the gray-level co-occurrence matrix of the anatomical image may be determined, and the autocorrelation feature image of the anatomical image can be obtained according to the gray-level co-occurrence matrix of the anatomical image.

Wherein, when determining the gray-level co-occurrence matrix of the anatomical image, the gray-level of pixels in the anatomical image can be quantized, and then, initial gray-level co-occurrence matrix in each setting direction of the anatomical image that its gray-level has been quantized can be obtained according to the set step size and direction, and the obtained initial gray-level co-occurrence matrix is normalized to obtain the normalized gray-level co-occurrence matrix, and the autocorrelation feature image of the anatomical image is determined according to the autocorrelation feature values of the normalized gray-level co-occurrence matrix.

The process for determining the autocorrelation feature image of the above anatomical image will be described below in conjunction with specific embodiments.

In one embodiment, $P(v_g, v_k)$ can be used to represent the gray-level co-occurrence matrix of an anatomical image. $P(v_g, v_k)$ can be obtained by calculating the probability that a pixel pair with image gray values of $v_g$ and $v_k$ appear in a certain direction in the case of the set step size d.

When determining the autocorrelation feature image of the above anatomical image, the above-mentioned anatomical image (or a specific or designated area of the above-mentioned anatomical image) can be quantized first, and quantized to a specified gray-level, such as $N_g$ gray-level; then, the pixel value of the above-mentioned anatomical image is mapped to the range $[1, N_g]$. At this time, the size of the gray-level co-occurrence matrix, namely $P(v_g, v_k)$ is $[N_g, N_g]$. As can be known that the scale of gray-level of image quantized determines the size of the corresponding gray-level co-occurrence matrix.

Figure 2:
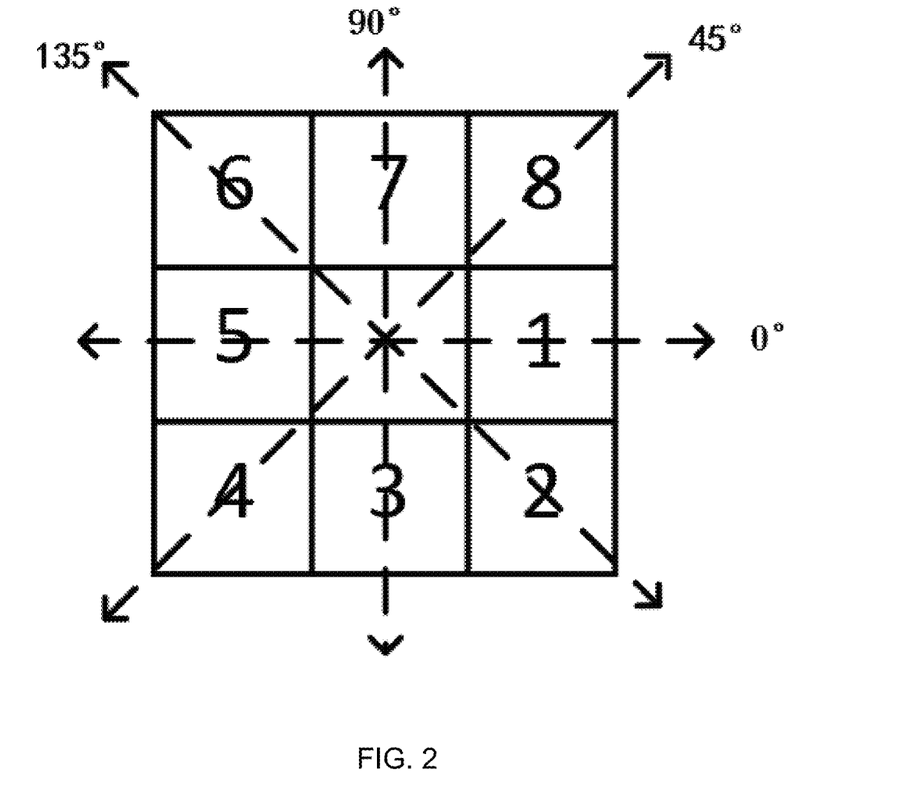
FIG. 2 is a schematic diagram of a pixel pair orientation of a gray-level co-occurrence matrix provided by an embodiment of the present disclosure.
Figure 3:
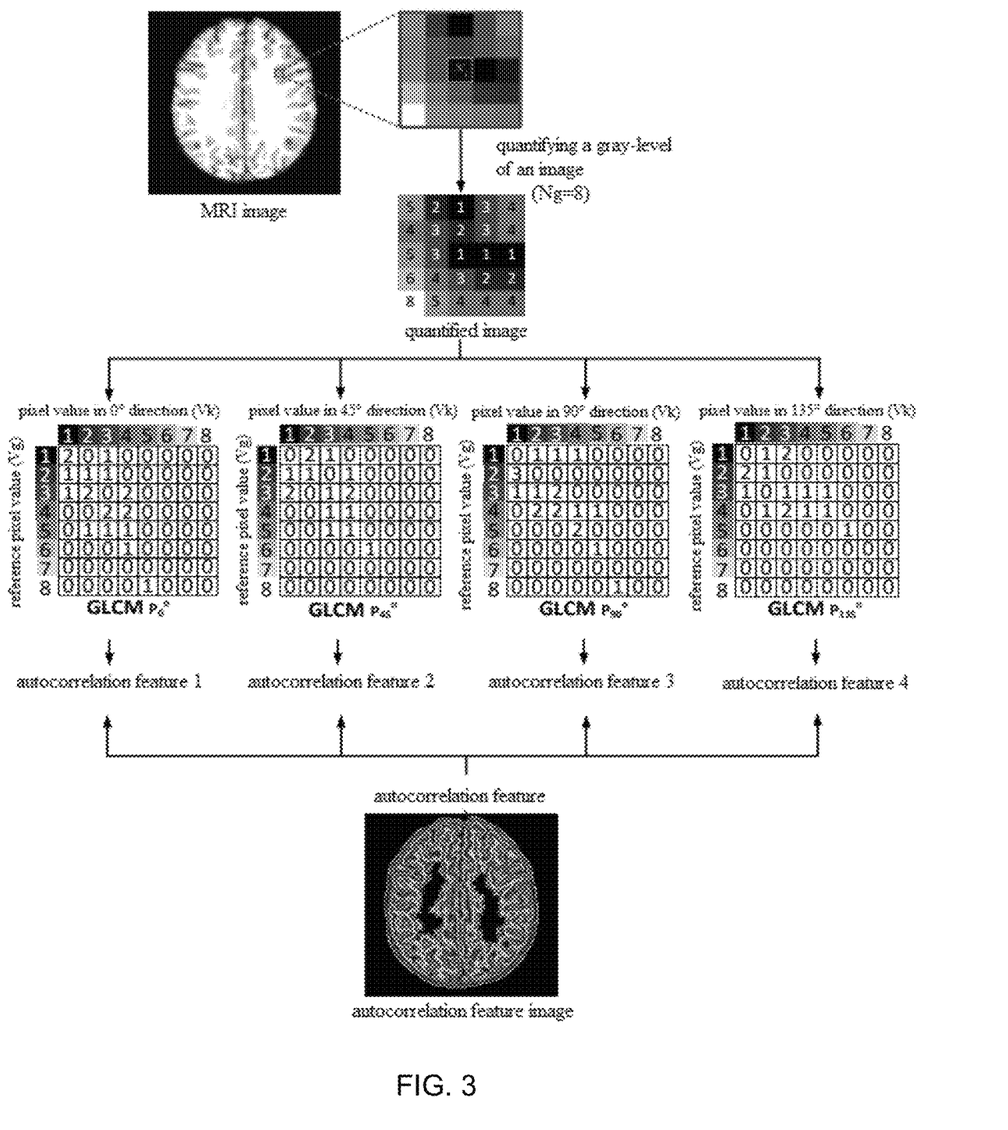
FIG. 3 is a schematic flowchart of a process for determining an autocorrelation feature image of a MRI image provided by an embodiment of the present disclosure.

After quantizing the pixel value of the above-mentioned anatomical image, the step size and direction of the pixel pair can be set. When setting the step size d, the step size d can be set to 1; when setting the direction, considering that there are 8 directions for the pixel pair, as shown in FIG. 2, namely horizontal (i.e., 0°), vertical (i.e., 90°), diagonal lines (i.e., 45° and 135°), and the opposite directions of these three directions, and the number of the pixel pairs $(V_g, V_k)$ and $(V_g, V_k)$ occurring in the opposite directions is the same. Therefore, the gray-level co-occurrence matrix in four directions (namely 0°, 45°, 90° and 135°) as shown in FIG. 2 can only be calculated, and the gray-level co-occurrence matrix in these four directions can be represented by using $P_0°$, $P_{45}°$, $P_{90}°$ and $P_{135}°$, respectively, as shown in FIG. 3.

In this embodiment, $(V_g, V_k)$ element value of $P_0°$ can be obtained by calculating the number of the pixel pair $(V_g, V_k)$ occurring in the 0° direction; correspondingly, element values of $P_{45}°$, $P_{90}°$ and $P_{135}°$ can be obtained by calculating the number of the pixel pair $(V_g, V_k)$ occurring in 45°, 90° and 135° directions, respectively.

After obtaining $P_{45}°$, $P_{90}°$ and $P_{135}°$, the four gray-level co-occurrence matrices can be normalized to obtain the normalized gray-level co-occurrence matrix.

In an embodiment, the normalized formula may be shown in the following formula.

$$p = \frac{P}{\sum_{v_g=1}^{N_g} \sum_{v_k=1}^{N_g} \frac{P(v_g, v_k)}{N_g^2}}$$

wherein, P can be the gray-level co-occurrence matrix before normalization, such as $P_0°$, $P_{45}°$, $P_{90}°$ and $P_{135}°$. P can be the gray-level co-occurrence matrix after normalization.

As shown in FIG. 3, after obtaining the normalized gray-level co-occurrence matrix, the autocorrelation feature value of the normalized gray-level co-occurrence matrix can be obtained, so as to determine an autocorrelation feature image of the above-mentioned anatomical image according to the obtained autocorrelation feature value.

In an embodiment, after obtaining the normalized gray-level co-occurrence matrix, the autocorrelation feature of the normalized gray-level co-occurrence matrix can be calculated according to the preset autocorrelation feature value calculation formula.

In an embodiment, the preset autocorrelation feature value calculation formula may be shown in the following formula.

$$f_a = \sum_{v_g=1}^{N_g} \sum_{v_k=1}^{N_g} \left(\frac{v_g}{N_g} \cdot \frac{v_k}{N_g}\right) \frac{p(v_g, v_k)}{N_g^2}$$

Wherein, $f_a$ represents the autocorrelation feature value; $N_g$ represents the gray-level; $V_g$ and $V_k$ represent gray values of an image; $P(v_g, v_k)$ represents gray-level co-occurrence matrix of the pixel pair $(V_g, V_k)$ after normalization.

After calculating the autocorrelation feature values of the above four directions (namely 0°, 45°, 90° and 135°), respectively, according to the above preset autocorrelation feature value calculation formula, as shown in FIG. 3, the average value of the autocorrelation feature values in the four directions is used as the autocorrelation texture feature of the anatomical image, and the autocorrelation feature image is generated according to the autocorrelation textual feature.

After acquiring the autocorrelation image of the anatomical image, the prior image can be acquired based on the above anatomical image and the autocorrelation feature image of the anatomical image.

In this embodiment, after acquiring the prior image, the feature value of the prior image can be acquired.

In an embodiment, the feature value of the prior image may be a matrix.

In this embodiment, the feature value of the prior image can be determined according to the radial Gaussian kernel function. In an embodiment, the radial Gaussian kernel function can be shown in the following formula.

$$K(f_j, f_{j'}) = \exp\left(\frac{-\|f_j - f_{j'}\|^2}{\sigma^2}\right)$$

Wherein, K represents the feature value of the prior image; j' represents a pixel in the neighborhood of pixel j; pixel j represents any pixel in the prior image; a represents the width parameter of the radial Gaussian kernel function.

In this embodiment, the feature value K of the prior image may be a kernel matrix, and may have multiple representation forms.

In this embodiment, after obtaining the feature value K of the prior image, K nearest neighbor pixels of each pixel may be obtained using the k nearest neighbor method, and the sparse kernel matrix K is then obtained.

After acquiring the feature value of the prior image, the PET image can be reconstructed according to the feature value and an iterative algorithm.

In an embodiment, the feature value of the prior image may be obtained by mapping an initial low-dimensional feature value to a high-dimensional space, wherein the initial low-dimensional feature value may be extracted from the prior image according to the kernel method, and the initial low-dimensional feature value can be used to describe each pixel in the prior image. In this embodiment, the feature value of the prior image can be used to linearly describe the pixel value of each pixel in the prior image.

In an embodiment, the target formula may be determined according to a preset pixel gray value calculation formula and the feature value obtained above.

In an embodiment, the pixel gray value calculation formula may be shown in the following formula.

$$x_j = \Sigma_{j'=1}^{N} \alpha_{j'} \cdot K(f_j, f_{j'})$$

In the preset pixel gray value calculation formula, j represents any pixel in the prior image; j' represents a pixel in the neighborhood of pixel j; $x_j$ represents the image gray value at pixel j; N represents the number of neighborhood pixels; $f_j$ and $f_{j'}$ represent the values of pixels j and j' in the prior image, respectively; $\alpha_{j'}$ represents the specified parameter value at pixel j'; K represents the feature value of the prior image.

From the pixel gray value calculation formula and feature value, it can be known that the target formula can be x=Kα. It can be known from the above contents that in the target formula, the feature value K has been obtained by the above steps, so the feature value K is known, and the image x and the designated parameter α are unknown.

In the embodiment of the present disclosure, the designated parameter may be a coefficient image parameter, and $\alpha_{j'}$ may represent the coefficient image at the pixel j', wherein the coefficient image may comprise an image corresponding to a preset coefficient.

In this embodiment, when reconstructing the PET image according to the feature value and the iterative algorithm, the acquired feature value can be added to the orthographic projection model of the PET image to obtain the target orthographic projection model and the target log-likelihood function corresponding to the target orthographic projection model, then the estimated value of the specified parameter in the target log-likelihood function can be obtained through an iterative formula according to the expectation maximization method, and the reconstructed PET image is determined according to the target formula, the feature value obtained above and the estimated value of the specified parameter.

In an embodiment, the PET projection data y can satisfy the Poisson distribution expected to be $\bar{y}$. In this case, the following log-likelihood function can be obtained by modeling.

$$L(y|x) = \Sigma_{i=1}^{n_i} \log \bar{y}_i - \log y_i!$$

wherein, x can represent the image to be reconstructed. $\bar{y}$ and x can have the following mapping relationship.

$$\bar{y} = Gx + r$$

$$G = \{g_{ij}\} \in R^{n_i \times n_j}$$

Wherein, $n_i$ and $n_j$ can represent the number of pixels and the number of detector pairs, respectively. The element $g_{ij}$ of the PET system matrix G may represent the probability that the photon pair emitted from the pixel j is detected by the detector pair i, and r can represent random events and scattering events.

In an implementation, after adding the acquired feature value K to the orthographic projection model of the PET image, the obtained orthographic projection model of the target may be as shown in the following equation.

$$\bar{y} = GK\alpha + r$$

Correspondingly, the target log-likelihood function corresponding to the target orthographic projection model can be as shown in the following formula.

$$\hat{\alpha} = \underset{\alpha \geq 0}{\mathrm{argmax}} L(y \mid K\alpha)$$

Then, the currently widely used expectation maximization method can be used to obtain the estimated value of the coefficient image through an iterative formula.

In an embodiment, the iteration formula may be shown in the following formula.

$$\alpha^{n+1} = \frac{\alpha^n}{K^T G^T 1}\left(K^T G^T \frac{y}{GK\alpha^n + r}\right)$$

After obtaining the estimated value $\hat{\alpha}$ of the coefficient image in the target log-likelihood function through the above iterative formula according to the expectation maximization method, the obtained coefficient image estimated value $\hat{\alpha}$ and the feature value K obtained above can be brought into the above target formula, and the reconstructed image is obtained.

At this time, the reconstructed PET image can be shown in the following formula.

$$\hat{x} = K\hat{\alpha}$$

It can be known from the above contents that the spatial texture features and gray-level features of the anatomical image MRI are combined in this embodiment, and the prior information is applied to the PET image reconstruction. Therefore, for the reconstruction of PET data with low counts, the signal-to-noise ratio of the reconstructed PET image and the accuracy of tumor image reconstruction are improved, thereby obtaining a PET image that satisfies the needs of clinical diagnosis.

Figure 4:
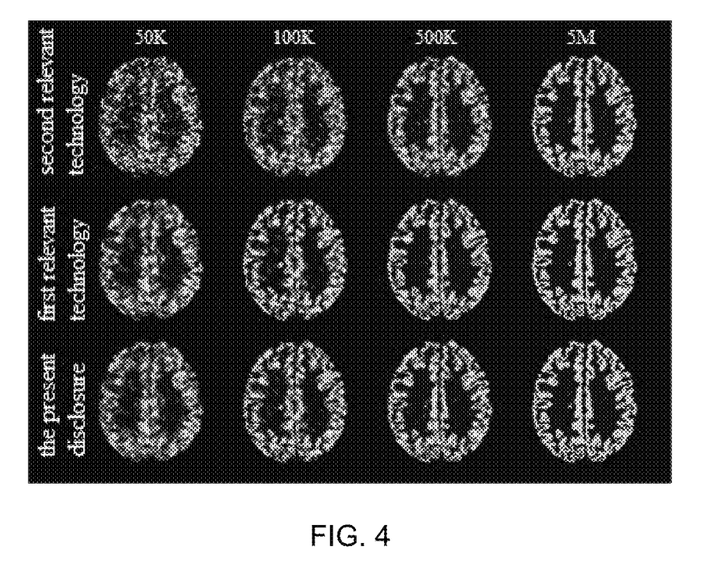
FIG. 4 is one of the application scenario diagrams of a method for reconstructing a PET image provided by an embodiment of the present disclosure.

With reference to FIG. 4, the two related technologies involved in this embodiment and the background art have been verified by simulation phantom data set experiments to obtain verification results under 50K, 100K, 500K, and 5M count conditions. It can be known from FIG. 4 that this embodiment can improve the signal-to-noise ratio of the image during low-count reconstruction.

Figure 5:
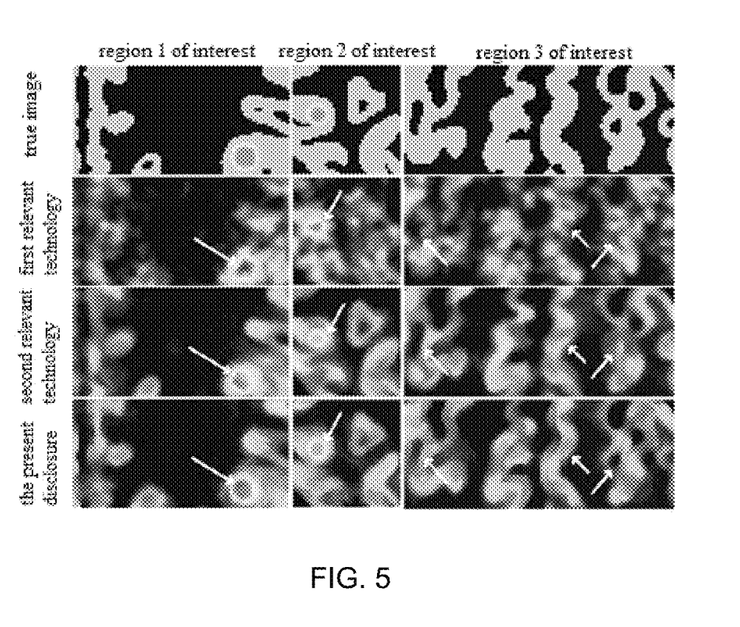
FIG. 5 is the second application scenario diagram of a method for reconstructing a PET image provided by an embodiment of the present disclosure.

With reference to FIG. 5, FIG. 5 is an enlarged view of regions of interest of the reconstructed PET image under the 500K count condition of the two related technologies involved in the embodiment and the background art. It can be known from FIG. 5 that the reconstruction of large tumors and small tumors is more accurate in this embodiment, and the degree of restoration of image details is improved.

With reference to Table 1 and Table 2, Table 1 and Table 2 are the deviation data and variance data of the reconstructed image under different count conditions of the two related technologies involved in the embodiment and the background art. It can be known from Table 1 and Table 2 that when this embodiment is applied in the reconstruction of PET data counted at each data level, the deviation of the reconstructed PET image is relatively small. In particular, as the count decreases, the advantages of the deviation and variance of the reconstructed image are gradually apparent, showing better reconstruction results for low count.

TABLE 1

| Count | Method | Full Image | Region 1 of interest | Region 2 of interest | Region 3 of interest |
|---|---|---|---|---|---|
| 50K | MLEM + filtration | 0.5706 | 0.5733 | 0.6052 | 0.6265 |
|  | kernel method | 0.4807 | 0.4537 | 0.4813 | 0.5366 |
|  | the disclosure | 0.4571 | 0.4258 | 0.4540 | 0.5061 |
| 100K | MLEM + filtration | 0.4874 | 0.4596 | 0.5376 | 0.5324 |
|  | kernel method | 0.4075 | 0.3753 | 0.4452 | 0.4284 |
|  | the disclosure | 0.3910 | 0.3545 | 0.4097 | 0.4217 |
| 500K | MLEM + filtration | 0.3962 | 0.3521 | 0.4471 | 0.4033 |
|  | kernel method | 0.3142 | 0.2793 | 0.3430 | 0.3402 |
|  | the disclosure | 0.3101 | 0.2757 | 0.3282 | 0.3053 |
| 5M | MLEM + filtration | 0.2893 | 0.2506 | 0.3154 | 0.3083 |
|  | kernel method | 0.2045 | 0.1754 | 0.2158 | 0.2217 |
|  | the disclosure | 0.2064 | 0.1749 | 0.2118 | 0.2236 |

TABLE 2

| Count | Method | Full Image | Region 1 of interest | Region 2 of interest | Region 3 of interest |
|---|---|---|---|---|---|
| 50K | MLEM + filtration | 0.6731 | 0.6777 | 0.7386 | 0.7378 |
|  | kernel method | 0.4693 | 0.4011 | 0.4703 | 0.4654 |
|  | the disclosure | 0.4114 | 0.3609 | 0.4248 | 0.4295 |
| 100K | MLEM + filtration | 0.4634 | 0.4779 | 0.5833 | 0.5410 |
|  | kernel method | 0.3444 | 0.3315 | 0.3900 | 0.3498 |
|  | the disclosure | 0.3236 | 0.2856 | 0.3390 | 0.3229 |
| 500K | MLEM + filtration | 0.3254 | 0.2557 | 0.4545 | 0.3470 |
|  | kernel method | 0.2170 | 0.1780 | 0.2953 | 0.2166 |
|  | the disclosure | 0.2133 | 0.1843 | 0.2699 | 0.2036 |
| 5M | MLEM + filtration | 0.2092 | 0.1613 | 0.2383 | 0.2234 |
|  | kernel method | 0.1068 | 0.0818 | 0.1103 | 0.1196 |
|  | the disclosure | 0.1099 | 0.0818 | 0.1013 | 0.1202 |

It can be known from the above contents that in the embodiments of the present disclosure, when reconstructing the PET image based on the prior image, the gray-level feature and the spatial texture feature of the MRI image are combined through the gray-level co-occurrence matrix. Therefore, more accurate texture features can be obtained by carry out calculation using fewer quantified gray-levels for the small image area, thereby effectively improving the quality of the reconstructed image and reducing the noise of the reconstructed image.

Figure 6:
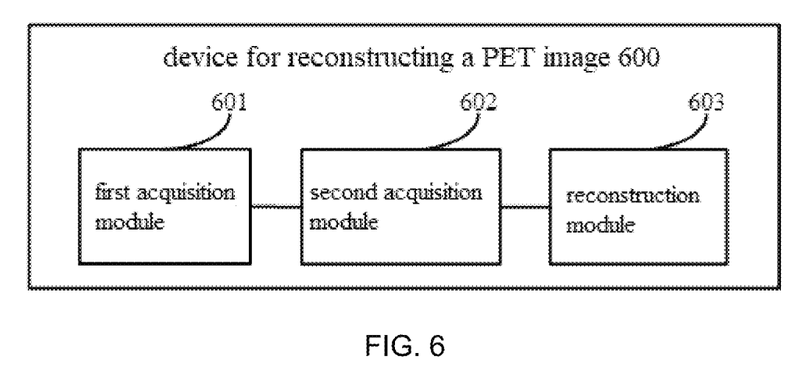
FIG. 6 is a schematic diagram of the module composition of a device 600 of reconstructing a PET image provided by an embodiment of the present disclosure.

Corresponding to the aforementioned PET image reconstruction method, an embodiment of the present disclosure also provides a PET image reconstruction device. As shown in FIG. 6, a reconstruction device 600 of the PET image comprises:

a first acquisition module 601 configured to acquire a prior image comprising an anatomical image and an autocorrelation feature image, and the autocorrelation feature image being determined based on a gray-level co-occurrence matrix of the anatomical image;

a second acquisition module 602 configured to acquire a feature value of the prior image; and a reconstruction module 603 configured to reconstruct the PET image according to the feature value and an iterative algorithm.

Optionally, the first acquisition module 601 is configured to quantize the gray-levels of pixels in the anatomical image, obtain the initial gray-level co-occurrence matrix of the gray-quantized anatomical images in each setting direction according to the set step size and direction, obtain a normalized gray-level co-occurrence matrix by normalizing the initial gray-level co-occurrence matrix, determine the autocorrelation feature image of the anatomy image according to the autocorrelation feature value of the normalized gray-level co-occurrence matrix, and acquire the prior image according to the anatomical image and the autocorrelation feature image of the anatomical image.

Optionally, the autocorrelation feature value of the normalized gray-level co-occurrence matrix is obtained by carrying out calculation according to a preset autocorrelation feature value calculation formula; the preset autocorrelation feature value calculation formula is the following formula Shown.

$$f_a = \sum_{v_g=1}^{N_g} \sum_{v_k=1}^{N_g} \left(\frac{v_g}{N_g} \cdot \frac{v_k}{N_g}\right) \frac{p(v_g, v_k)}{N_g^2}$$

wherein, $f_a$ represents the autocorrelation feature value; $N_g$ represents the gray-level; $v_g$ and $v_k$ represent the image gray value; $P(v_g, v_k)$ represents the normalized gray-level co-occurrence matrix of the pixel pair $(v_g, v_k)$.

Optionally, the feature value of the prior image is obtained by mapping the initial low-dimensional feature value to a high-dimensional space; the initial low-dimensional feature value is extracted from the prior image according to a kernel method; the feature value of the prior image is used to linearly describe the pixel value of each pixel in the prior image.

Optionally, the second acquisition module 602 is configured to determine the feature value of the prior image according to a radial Gaussian kernel function; wherein, the radial Gaussian kernel function is shown in the following formula.

$$K(f_j, f_{j'}) = \exp\left(\frac{-\|f_j - f_{j'}\|^2}{\sigma^2}\right),$$

wherein j' represents a pixel in the neighborhood of pixel j; $x_j$ Represents the image gray value at pixel j; N represents the number of neighborhood pixels; $f_j$ and $f_{j'}$ represent the values of pixels j and j' in the prior image, respectively; $\alpha_{j'}$ represents the preset coefficient image at the pixel j'; K represents the feature value of the prior image.

wherein, K represents the feature value of the prior image; j' represents a pixel in the neighborhood of pixel j; the pixel j represents any pixel in the prior image; σ represents the width parameter of the radial Gaussian kernel function.

Optionally, the reconstruction module 603 is configured to add the feature value to the orthographic projection model of the PET image to obtain the target orthographic projection model and the target log-likelihood function corresponding to the target orthographic projection model, obtain the estimated value of the specified parameter in the target log-likelihood function through an iterative formula according to the expectation maximization method, and determine the reconstructed PET image according to the target formula, the feature value, and the estimated value of the specified parameter; wherein, the target formula is determined through the feature value and the pixel gray value calculation formula.

Optionally, the pixel gray value calculation formula is shown in the following formula.

$$x_j = \sum_{j'=1}^{N} \alpha_{j'} \cdot K(f_j, f_{j'})$$

Where j represents any pixel in the prior image; j' represents a pixel in the neighborhood of pixel j; $x_j$ represents the image gray value at pixel j; N represents the number of pixels in the neighborhood; $x_j$ and $f_{j'}$ represent the values of pixels j and j' in the prior image, respectively; $\alpha_{j'}$ represents the specified parameter value at the pixel j'; K represents the feature value of the prior image.

Correspondingly, the target formula is: x=Kα.

When the PET image is reconstructed based on the prior image, the gray-level feature and spatial texture feature of the MRI image are combined through the gray-level co-occurrence matrix. Therefore, more accurate texture features can be obtained by carry out calculation using fewer quantized gray-levels for the small image area, thereby effectively improving the quality of the reconstructed image and reducing the noise of the reconstructed image.

Figure 7:
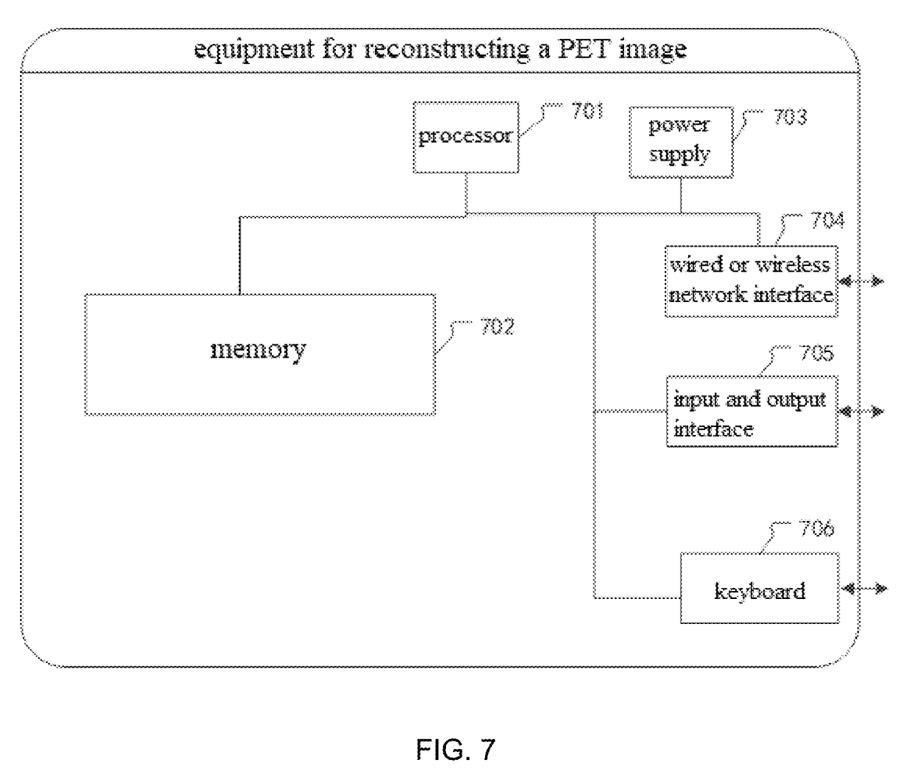
FIG. 7 is a schematic diagram of a hardware structure for an equipment of reconstructing a PET image provided by an embodiment of the present disclosure.

Corresponding to the above-mentioned PET image reconstruction method, a PET image reconstruction equipment is also provided in an embodiment of the present disclosure. FIG. 7 is a schematic diagram of the hardware structure of the PET image reconstruction equipment provided by an embodiment of the present disclosure.

The PET image reconstruction equipment may be a terminal device or a server for reconstructing a PET image provided in the foregoing embodiment.

The PET image reconstruction equipment may have relatively large differences due to different configurations or performances, and may comprise one or more processors 701 and a memory 702, and the memory 702 may store one or more application program or data. Wherein, the memory 702 may be short-term storage or persistent storage. The application program stored in the memory 702 may comprise one or more modules (not shown in the FIGS.), and each module may comprise a series of computer-executable instructions in the PET image reconstruction equipment. Furthermore, the processor 701 may be configured to communicate with the memory 702, and execute a series of computer-executable instructions in the memory 702 on the PET image reconstruction equipment. The PET image reconstruction equipment may also comprise one or more power supplies 703, one or more wired or wireless network interfaces 704, one or more input and output interfaces 705, and one or more keyboards 706.

Specifically, in this embodiment, the PET image reconstruction equipment comprises a memory and one or more programs, and the one or more programs are stored in the memory, and the one or more programs may comprise one or more modules, and each module may comprise a series of computer-executable instructions in the PET image reconstruction equipment, and is configured to be executed by one or more processors to execute the above-mentioned embodiments.

When reconstructing the PET image based on the prior image, the gray-level feature and spatial texture feature of the MRI image are combined through the gray-level co-occurrence matrix. Therefore, more accurate texture features can be obtained by carry out calculation using fewer quantized gray-levels for the small image area, thereby effectively improving the quality of the reconstructed image and reducing the noise of the reconstructed image.

The embodiment of the present disclosure also provides a computer-readable storage medium storing a computer program that, when the computer program is executed by a processor, implements the steps of any one of the above methods.

In addition, a computer program product is also provided in the embodiment of the present disclosure, the computer program product comprises a computer program stored on a non-transitory computer-readable storage medium, and the computer program comprises program instructions that, when executed by a computer, make the computer to execute the method in any of the foregoing method embodiments.

In the 1990s, improvements in a technology can be clearly divided into hardware improvements (e.g. improvements in circuit structures such as diodes, transistors, switches etc.) or software improvements (improvements in method processes). However, with the development of the technology, the improvements of many of today's method processes can also be considered as direct improvements of the hardware circuit structures. Almost all designers may get the corresponding hardware circuit structure by programming the improved method process into the hardware circuit. Therefore, it cannot be said that the improvement of a method process cannot be realized by a hardware entity module. For example, a Programmable Logic Device (PLD) (for example, a Field Programmable Gate Array (FPGA)) is such an integrated circuit whose logical function is determined by user programming for the device. By the designer's own programming to "integrate" a digital system on a PLD, it is not need to require the chip manufacturer to design and manufacture a dedicated integrated circuit chip. Moreover, today, instead of manually manufacturing integrated circuit chips, this type of programming is mostly implemented using "logic compiler" software, which is similar to the software compiler used in general program development, however before compiling, the original code has to be written in a specific programming language, which is called hardware description language (HDL), and HDL is not only one kind, but there are many kinds, such as ABEL (Advanced Boolean Expression Language), AHDL (Altera Hardware Description Language), Confluence, CUPL (Cornell University Programming Language), HDCal, JHDL (Java Hardware Description Language), Lava, Lola, MyHDL, PALASM, RHDL (Ruby Hardware Description Language) etc., currently, the most commonly used HDL is VHDL (Very-High-Speed Integrated Circuit Hardware Description Language) and Verilog. It should also be apparent to a person skilled in the art that a hardware circuit implementing some logic method processes can be readily acquired by simply logic programming for the method processes using the above listed hardware description languages and programming them into the integrated circuit.

The controller may be implemented in any suitable manner, for example, the controller may be a microprocessor or processor, a computer-readable medium for storing computer-readable program codes (e.g. software or firmware) that can be executed by the (micro)processor, logic gate, switch, application specific integrated circuit (ASIC), programmable logic controller and embedded microcontroller, the controller comprises but is not limited to the following microcontrollers: ARC 625D, Atmel AT91SAM, Microchip PIC18F26K20 and Silicon Labs C8051F320, the memory controller can also be implemented as a part of the memory control logic. A person skilled in the art should also know that, besides implementing the controller only in the manner of a computer-readable program code, by logic programming for the method processes, the controller is enabled to implement same functions in the manner of logic gate, switch, ASIC, programmable logic controller and embedded microcontroller. Therefore, such a controller may be regarded as a hardware component, and devices included therein for archiving various functions may also be regarded as structures within the hardware component. Or even the device for archiving various functions may be regarded not only as a software module but also a structure within a hardware component for implementing method.

The system, device, module or unit set forth in the above embodiments may be specifically implemented by a computer chip or an entity, or may be implemented by a product having a certain function. A typical implementation device is a computer. Specifically, the computer may be, for example, personal computer, laptop computer, cellular phone, camera phone, smart phone, personal digital assistant, media player, navigation device, email device, game console, tablet computer, wearable device, or combinations of any of these devices.

For the convenience of description, the above devices are divided into various units according to their functions and described separately. Of course, the functions of the units may be implemented in the same one or more software and/or hardware when implementing the disclosure.

A person skilled in the art should know that embodiments of the present disclosure may be implemented as a method, a system, or a computer program product. Therefore, the present disclosure may take the form of an entirely hardware embodiment, an entirely software embodiment, or an embodiment combining software and hardware. Furthermore, the present disclosure may take the form of a computer program product embodied on one or more computer usable storage mediums (comprising but not limited to disk storage, CD-ROM, optical memory, etc.) containing computer usable program code embodied therein.

The present disclosure is described with reference to flow chart and/or block diagrams of the method, the device (system), and the computer program product according to the embodiments of the present disclosure. It should be understood that each flow and/or block in the flowcharts and/or block diagrams, and combinations of the flows and/or blocks in the flowcharts and/or block diagrams may be implemented by computer program instructions. The computer program instructions may be provided to a processor of a general purpose computer, of a special purpose computer, of an embedded processor, or of other programmable data processing device to generate a machine, so that the instructions executed by the processor of the computer or of other programmable data processing device generate a device for archiving the functions specified in one or more flow step of a flowchart and/or one or more block of block diagrams.

The computer program instructions may also be stored in a computer-readable memory capable of directing a computer or other programmable data processing device to operate in a specific manner, so that the instructions stored in the computer-readable memory generate an article of manufacture comprising the command device, the command device archives the functions specified in one or more flow step of a flowchart and/or one or more block of block diagrams.

The computer program instructions may also be loaded to a computer or other programmable data processing device, so that a series of operation steps can be performed on the computer or other programmable device to generate a computer implemented process, and thus the instructions executed on a computer or other programmable data processing device provide the steps for archiving the functions specified in one or more flow steps of a flowcharts and/or one or more blocks of block diagrams.

In a typical configuration, the computing device comprises one or more processors (CPUs), input/output interface, network interface and memory.

The memory may include volatile memory, random access memory (RAM) and/or non-volatile memory, such as read only memory (ROM) or flash memory (flash RAM), in a computer-readable medium. The memory is an example of computer-readable mediums.

The computer-readable medium comprises permanent and non-permanent, removable and non-removable medium, on which information storage may be implemented by any method or technology. The information may be computer-readable instruction, data structure, module of an application program or other data. Examples of storage medium for computers include, but are not limited to, Phase Change Memory (PRAM), Static Random Access Memory (SRAM), Dynamic Random Access Memory (DRAM), other type of Random Access Memory (RAM), Read-Only Memory (ROM), Electrically Erasable Programmable Read Only Memory (EEPROM), flash memory or other memory technology, CD-ROM, DVD or other optical storage, magnetic tape cartridge, tape magnetic disk storage or other magnetic storage device, or any other non-transport medium, which may be used to store information that may be accessed by a computing device. As defined herein, the computer-readable medium does not include transitory medium, such as modulated data signal and carrier wave.

It should also be noted that the terms "include", "comprise" or any other variations thereof are intended to cover non-exclusive inclusions, such that processes, methods, articles or devices that include a series of elements include not only those elements but also include other elements that are not explicitly listed, or include elements that are inherent to such processes, methods, articles or devices. In the case of no more limitation, the element defined by the sentence "comprises a . . . " does not exclude the existence of another identical element in the processes, methods, articles or devices comprising such element.

It should be understood by a person skilled in the art that embodiments of the present disclosure may be implemented as methods, systems or computer program products. Therefore, the present disclosure may take the form of an entirely hardware embodiment, an entirely software embodiment or an embodiment combining software and hardware aspects. Furthermore, the present disclosure can be implemented in the form of a computer program product implemented on one or more computer usable storage media (comprising but not limited to disk storage, CD-ROM, optical memory, etc.) containing computer usable program codes embodied therein.

The disclosure may be described in the general context of computer-executable instructions executed by computer, such as program module. Generally, program module comprises routine, program, object, component, data structure and so on that performs particular task or implements particular abstract data type. The disclosure may also be practiced in a distributed computing environment, wherein tasks are performed by remote processing devices that are connected via a communications network. In a distributed computing environment, program modules may be located in both local and remote computer storage mediums comprising storage devices.

Each embodiment in this specification is described in a progressive manner, the same or similar parts among the embodiments can be referred to each other, and each embodiment focuses on the difference from other embodiments. In particular, for the system embodiment, since it is basically similar to the method embodiment, the description thereof is relatively simple, and the related parts may refer to that of the method embodiment.

The above description is only illustrative example of the disclosure and is not intended to limit the disclosure. For a person skilled in the art, the disclosure may have various changes and variations. Any modification, equivalent replacement, and improvement made within the spirit and principle of the disclosure should fall in the scope of the claims of the disclosure.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for reconstructing a Positron Emission Tomography (PET) image, comprising the steps of:
   acquiring a prior image comprising an anatomical image and an autocorrelation feature image, the autocorrelation feature image being determined based on a gray-level co-occurrence matrix of the anatomical image;
   acquiring a feature value of the prior image; and
   reconstructing the PET image according to the feature value and an iterative algorithm;
   wherein said step of reconstructing the PET image according to the feature value and the iterative algorithm comprises:
   adding the feature value to an orthographic projection model of the PET image to obtain a target orthographic projection model and a target log-likelihood function corresponding to the target orthographic projection model;
   obtaining an estimated value of a specified parameter in the target log-likelihood function through an iterative formula according to an expectation maximization method; and
   determining the reconstructed PET image according to a target formula, the feature value, and the estimated value of the specified parameter; wherein the target formula is determined through the feature value and a pixel gray value calculation formula.

2. The method according to claim 1, wherein said step of acquiring the prior image comprises:
   quantizing gray-level of pixels in the anatomical image;
   obtaining an initial gray-level co-occurrence matrix of the gray-level quantized anatomical image in each setting direction according to a set step size and direction;
   normalizing the initial gray-level co-occurrence matrix to obtain a normalized gray-level co-occurrence matrix;
   determining the autocorrelation feature image of the anatomical image according to an autocorrelation feature value of the normalized gray-level co-occurrence matrix; and
   acquiring the prior image according to the anatomical image and the autocorrelation feature image of the anatomical image.

3. The method according to claim 2, wherein the autocorrelation feature value of the normalized gray-level co-occurrence matrix is calculated according to a preset autocorrelation feature value calculation formula; the preset autocorrelation feature value calculation formula is:

$$f_a = \frac{\sum_{v_g=1}^{N_g} \sum_{v_k=1}^{N_g} \left(\frac{v_g}{N_g} \cdot \frac{v_k}{N_g}\right) p(v_g, v_k)}{N_g^2}$$

wherein, $f_a$ represents the autocorrelation feature value; $N_g$ represents a gray-level; $v_g$ and $v_k$ represent image gray values; $P(v_g, v_k)$ represents a gray-level co-occurrence matrix obtained by normalizing a pair of pixels $(v_g, v_k)$.

4. The method according to claim 1, wherein the feature value of the prior image is obtained by mapping an initial low-dimensional feature value to a high-dimensional space; the initial low-dimensional feature value is extracted from the prior image according to a kernel method; the feature value of the prior image linearly describes a pixel value of each pixel in the prior image.

5. The method according to claim 4, wherein said step of acquiring the feature value of the prior image comprises:
   determine the feature value of the prior image according to a radial Gaussian kernel function; wherein, the radial Gaussian kernel function is:

$$K(f_j, f_{j'}) = \exp\left(\frac{-\|f_j - f_{j'}\|^2}{\sigma^2}\right)$$

wherein, K represents the feature value of the prior image; represents a pixel in the neighborhood of pixel j; the pixel j represents any pixel in the prior image; a represents a width parameter of the radial Gaussian kernel function.

6. The method according to claim 1, wherein the pixel gray value calculation formula is:

$$x_j = \sum_{j'=1}^{N} \alpha_{j'} K(f_j, f_{j'})$$

wherein j represents any pixel in the prior image; j' represents a pixel in the neighborhood of pixel j; $x_j$ represents an image gray value at pixel j; N represents the number of pixels in the neighborhood; $f_j$ and $f_{j'}$ represent values of pixels j and j' in the prior image, respectively; $\alpha_{j'}$ represents the specified parameter value at the pixel j'; K represents the feature value of the prior image;

correspondingly, the target formula is: $x=K\alpha$.

7. An equipment, comprising: a memory, a processor, and a computer program stored on the memory and executable by the processor, the computer program, when executed by the processor, implementing the steps of the method according to claim 1.

8. A non-transitory computer-readable medium storing a computer program that, when executed by a processor, implements the steps of the method according to claim 1.

* * * * *